United States Patent [19]
Forestier et al.

[11] Patent Number: 5,951,968
[45] Date of Patent: Sep. 14, 1999

[54] UV-PHOTOPROTECTIVE DIBENZOYLMETHANE COMPOSITIONS COMPRISING PHOTOSTABILIZING AMOUNTS OF BENZALMALONATE SILANES

[75] Inventors: Serge Forestier, Claye Souilly; Hervé Richard, Villepinte; Delphine Allard, Colombes; Didier Candau, Bievres, all of France

[73] Assignee: Societe L'Oreal S.A., Paris, France

[21] Appl. No.: 09/035,758

[22] Filed: Mar. 6, 1998

[30] Foreign Application Priority Data

Mar. 7, 1997 [FR] France ................... 97 02759

[51] Int. Cl.$^6$ ............... A61K 7/42; A61K 7/00; A61K 31/695; A61K 31/12
[52] U.S. Cl. ............ 424/59; 424/60; 424/400; 424/401; 514/63; 514/678; 514/685
[58] Field of Search ............... 424/59, 60, 400, 424/401; 514/63, 678, 685

[56] References Cited

U.S. PATENT DOCUMENTS

| | | | |
|---|---|---|---|
| 5,236,698 | 8/1993 | Richard et al. | 424/47 |
| 5,733,895 | 3/1998 | Forestier et al. | 514/63 |
| 5,776,440 | 7/1998 | Forestier et al. | 424/59 |
| 5,849,909 | 12/1998 | Richard et al. | 544/197 |

*Primary Examiner*—Shelley A. Dodson
*Attorney, Agent, or Firm*—Burns, Doane, Swecker & Mathis, L.L.P.

[57] ABSTRACT

Topically applicable, stable, UV-photoprotective cosmetic/dermatological compositions well suited for the photoprotection of human skin and/or hair against the damaging effects of UV-A and UV-B irradiation, comprise (a) an effective UV-photoprotecting amount of at least one dibenzoylmethane UV-sunscreen compound and (b) an effective dibenzoylmethane compound (a) photostabilizing amount of at least one benzalmalonate silane having the structural formula (I):

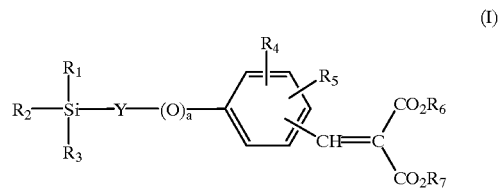

18 Claims, No Drawings

UV-PHOTOPROTECTIVE DIBENZOYLMETHANE COMPOSITIONS COMPRISING PHOTOSTABILIZING AMOUNTS OF BENZALMALONATE SILANES

CROSS-REFERENCE TO PRIORITY APPLICATION

This application claims priority under 35 U.S.C. §119 of FR-97/02759, filed Mar. 7, 1997, hereby expressly incorporated by reference.

BACKGROUND OF THE INVENTION

1. Technical Field of the Invention

The present invention relates to novel topically applicable UV-photoprotective compositions containing at least one normally photolabile dibenzoylmethane UV-screening compound and, as a photostabilizer therefor, an effective amount of at least one particular benzalmalonate silane.

This invention also relates to certain novel processes for the synthesis of said particular benzalmalonate silanes.

2. Description of the Prior Art

It is known to this art that light radiation of wavelengths ranging from 280 nm to 400 nm promote tanning of the human epidermis, and that radiation of wavelengths more particularly ranging from 280 to 320 nm, i.e., UV-B irradiation, causes erythemas and skin burns which are detrimental to the development of natural bronzing and tanning. For these reasons, as well as for aesthetic reasons, there is a constant demand for means to control this natural bronzing and thus control the coloration of the skin; it is thus advisable to filter such UV-B radiation from the skin.

It is also known to this art that UV-A irradiation, of wavelengths of from 320 to 400 nm, which promotes tanning of the skin, also adversely affects it, especially in the case of a sensitive skin or of a skin which is continuously exposed to solar radiation. The UV-A rays, in particular, cause a loss in the elasticity of the skin and the appearance of wrinkles, resulting in premature cutaneous aging. UV-A radiation promotes triggering of the erythematous reaction or amplifies this reaction in certain individuals and can even be the source of phototoxic or photoallergic reactions. Thus, for aesthetic and cosmetic reasons such as the preservation of the natural elasticity of the skin, for example, more and more individuals seek to control the effect of UV-A rays on their skin. It is thus desirable to also filter out UV-A radiation.

In this respect, one class of UV-A filters of particular interest comprises the dibenzoylmethane compounds, and especially 4-tert-butyl-4'-methoxydibenzoylmethane, which indeed have a great capacity for intrinsic absorption. These dibenzoylmethane compounds, which are per se well known as active filters in the UV-A region, are described, in particular, in FR-A-2,326,405 and FR-2,440,933, as well as in EP-A-0,114,607; 4-tert-butyl-4'-methoxydibenzoylmethane is also commercially available under the trademark "PARSOL 1789" by GIVAUDAN.

Unfortunately, the dibenzoylmethane derivatives are compounds which are relatively sensitive to ultraviolet radiation (especially UV-A irradiation), namely, they have an unfortunate tendency to degrade to a more or less rapid extent under the action of such radiation. Thus, this substantial lack of photochemical stability of dibenzoylmethane compounds with regard to ultraviolet radiation which by their very nature they are intended to be subjected, does not permit constant protection to be guaranteed during prolonged exposure to the sun, such that, in a restrictive fashion, repeated applications at regular and close intervals of time must be carried out by the user to provide an efficacious protection of the skin against UV rays.

The photostabilization of dibenzoylmethane compounds with respect to UV radiation remains a problem which to date has not satisfactorily been resolved.

Thus, EP-A-0,709,080 describes combining dibenzoylmethane derivatives with very specific benzalmalonate derivatives, namely, benzalmalonate siloxanes, in order to decrease the photoinstability of said dibenzoylmethane compounds. In particular, this '080 application mandates that the siloxane structure of these compounds is essential to provide satisfactory photostabilization (see page 10, line 22 of EP-A-0,709,080). However, these benzalmalonate siloxanes are molecules which are bulky and complex to synthesize.

SUMMARY OF THE INVENTION

It has now unexpectedly and surprisingly been determined that combining the dibenzoylmethane compounds indicated above with a photostabilizing effective amount, not of a benzalmalonate siloxane, but of a benzalmalonate silane, markedly enhances the photochemical stability (or photostability) of these same dibenzoylmethane compounds.

It has also been determined that certain novel processes for the preparation of various of these benzalmalonate silanes present the advantage of being much more easy to carry out than the hydrosilylation process described in the prior art, for example, in JP-07/330,779.

Thus, the present invention features improving the photostability of at least one photolabile dibenzoylmethane compound with respect to UV-radiation, by intimately combining said dibenzoylmethane compounds with an effective amount of at least one benzalmalonate silane having the following structural formula (I):

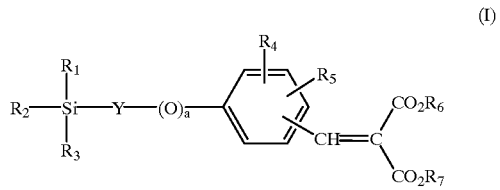

in which $R_1$, $R_2$ and $R_3$, which may be identical or different, are each an optionally halogenated $C_1$–$C_{10}$ alkyl radical or a phenyl radical; $R_4$ and $R_5$, which may be identical or different, are each a hydrogen atom, a hydroxyl radical, a $C_1$–$C_6$ alkyl radical, a $C_1$–$C_6$ alkoxy radical, or a trimethylsilyloxy radical; $R_6$ and $R_7$, which may be identical or different, are each a $C_1$–$C_8$ alkyl radical; a is equal to 0 or 1; and Y is a divalent radical having one of the following formulae (1) to (4):

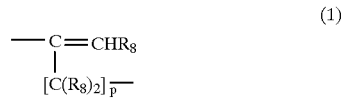

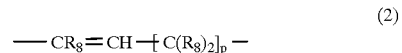

-continued

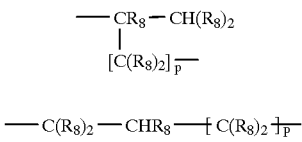

wherein $R_8$ is a hydrogen atom or a $C_1$–$C_5$ alkyl radical, and p is an integer ranging from 1 to 10, inclusive, with the proviso that the group —Y—(O)$_a$— and the two groups $R_4$ and $R_5$ are variously bonded to the aromatic ring member in the para-position and in the two meta-positions with respect to the radical —CH=C—[(CO$_2$R$_6$)](CO$_2$R$_7$).

DETAILED DESCRIPTION OF BEST MODE AND SPECIFIC/PREFERRED EMBODIMENTS OF THE INVENTION

More particularly according to the present invention, the subject cosmetic and/or dermatological compositions present the advantage of being particularly photostable, even after prolonged exposure to UV-A and UV-B radiation. This radiation can be of natural (sun) or artificial (UV lamp) origin. In addition, as described below, the benzalmalonate silanes being molecules which are quite easy to synthesize, the compositions according to the invention are likewise readily formulated industrially.

The present invention thus features the use of a benzalmalonate silane to enhance the stability with respect to UV rays of a dibenzoylmethane compound contained in a UV-screening cosmetic and/or dermatological composition.

As indicated above, the dibenzoylmethane derivatives that are photostabilized according to the present invention are compounds which are per se known to this art and are described in the abovementioned FR-A-2,326,405, FR-A-2,440,933 and EP-A-0,114,607.

According to the present invention, it is of course envisioned to employ one or more dibenzoylmethane compounds.

Particularly exemplary dibenzoylmethane compounds according to the present invention include the following:

2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane;
2,6-dimethyl-4-tert-butyl-4'-methoxydibenzoylmethane;
4,4'-dimethoxydibenzoylmethane.

Among the dibenzoylmethane compounds indicated above, preferred is 4-tert-butyl-4'-methoxydibenzoylmethane, especially that commercially available under the trademark "PARSOL 1789" by GIVAUDAN, this filter thus having the following structural formula:

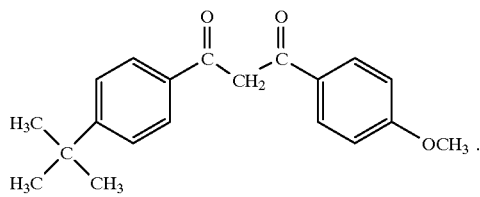

Another preferred dibenzoylmethane compound according to the present invention is 4-isopropyldibenzoylmethane, a filter marketed under the trademark "EUSOLEX 8020" by MERCK, and having the following structural formula:

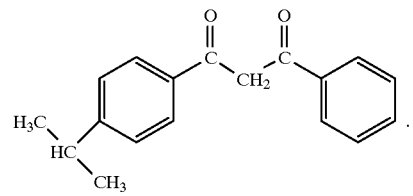

The dibenzoylmethane derivatives are advantageously present in the stabilized compositions according to the invention in amounts generally ranging from 0.01% to 10% by weight and preferably in amounts ranging from 0.3% to 5% by weight, with respect to the total weight of the composition.

As indicated above, the benzalmalonate silanes according to this invention are known compounds which are described, especially, in JP-07/330,779. These have the following structural formula (I):

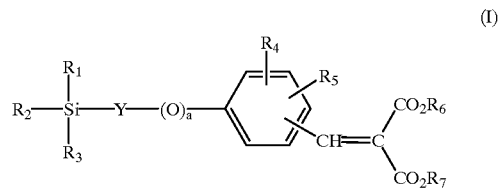

in which $R_1$, $R_2$ and $R_3$, which may be identical or different, are each an optionally halogenated $C_1$–$C_{10}$ alkyl radical or a phenyl radical; $R_4$ and $R_5$, which may be identical or different, are each a hydrogen atom, a hydroxyl radical, a $C_1$–$C_6$ alkyl radical, a $C_1$–$C_6$ alkoxy radical, or a trimethylsilyloxy radical; $R_6$ and $R_7$, which may be identical or different, are each a $C_1$–$C_8$ alkyl radical; a is equal to 0 or 1; and Y is a divalent radical having one of the following formulae (1) to (4):

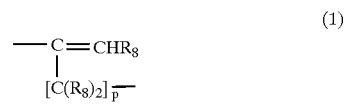

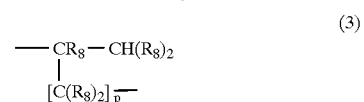

-continued

(4)

wherein $R_8$ is a hydrogen atom or a $C_1$–$C_5$ alkyl radical, and p is an integer ranging from 1 to 10, inclusive, with the proviso that the group —Y—(O)$_a$— and the two groups $R_4$ and $R_5$, are variously bonded to the aromatic ring member in the para-position and in the two meta-positions with respect to the radical —CH═C—[(CO$_2$R$_6$)](CO$_2$R$_7$).

The benzalmalonate silanes according to the invention, as will later be seen, present the advantage of being much more simple to synthesize and to purify than the benzalmalonate siloxanes known to the prior art. Too, the process of the invention is likewise easier to carry out on an industrial scale.

In a preferred embodiment of the invention, the silanes of formula (I) above and satisfying at least one, preferably all, of the following conditions are employed:

$R_1$ is methyl,
$R_2$ is methyl or ethyl,
$R_3$ is methyl,
Y is a divalent radical of formula (3) or (4) in which $R_8$ is hydrogen or methyl and p is 1 or 2,
a is 1,
$R_4$ is hydrogen or a methoxy radical,
$R_5$ is hydrogen,
$R_6$ is methyl or ethyl,
$R_7$ is methyl or ethyl,
the —Y—(O)$_a$— group is bonded to the aromatic ring member in the para-position with respect to the —CH═C—[(CO$_2$R$_6$)](CO$_2$R$_7$) radical.

Particularly suitable silanes according to the present invention are the compounds having the following structural formulae (5), (6) and (7):

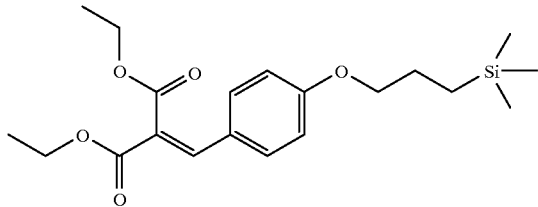
(5)

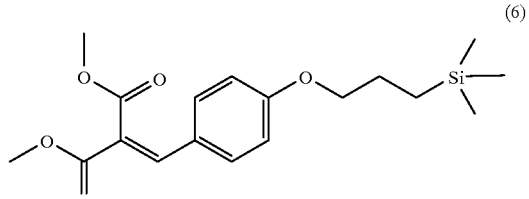
(6)

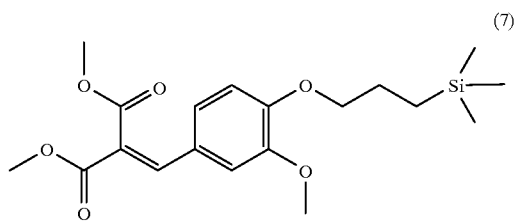
(7)

To prepare the compounds of formula (I) in which a=0, a hydrosilylation reaction is carried out between the corresponding unsaturated derivative and the corresponding silane such as is described in JP-07/330,779.

The present invention features a first process (reaction scheme A) for the preparation of the compounds of formula (I) in which a is 1, comprising, in a first step, reacting an aromatic hydroxybenzaldehyde of formula (8) below with a halogenated silane derivative of formula (9) below. Then, in a second step, the benzaldehyde of formula (10) thus obtained is condensed with a malonic diester of formula (11) below. Preferably, the aromatic hydroxybenzaldehyde and the halogenated silane derivative are reacted in the presence of a base according to a conventional alkylation reaction, the condensation of the benzaldehyde obtained with the malonic diester being carried out in toluene in the presence of piperidinium acetate as a catalyst (Knoevenagel condensation) according to the following reaction scheme:

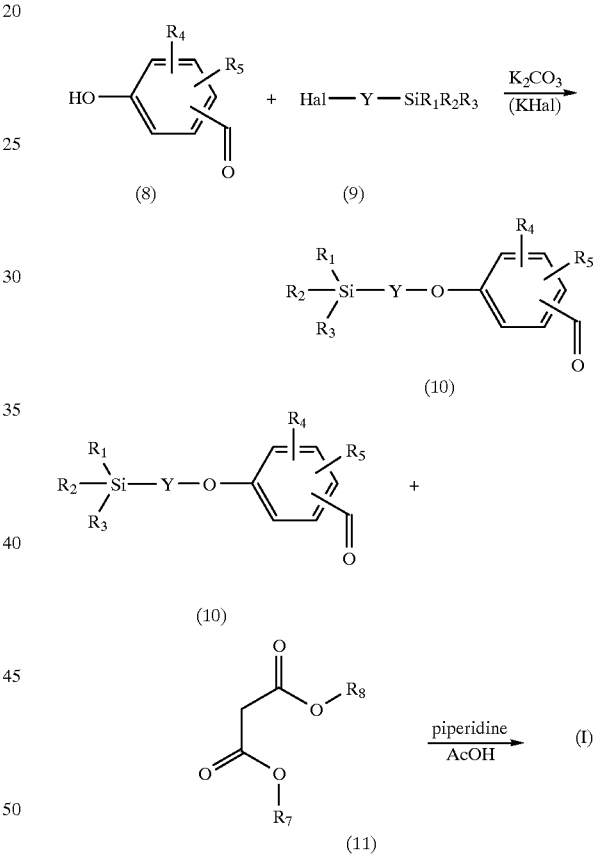

in which Y, $R_1$, $R_2$, $R_3$, $R_4$, $R_5$, $R_6$ and $R_7$ are as defined above for formula (I) and Hal is a halogen, preferably chlorine.

The present invention also features a second process (reaction scheme B) for the preparation of the compounds of formula (I) in which a is 1, comprising reacting a hydroxybenzalmalonate of formula (12) below with a halogenated silane derivative of formula (9). Preferably, the hydroxybenzalmalonate and the halogenated silane derivative are reacted in the presence of a base according to a conventional alkylation reaction according to the following scheme:

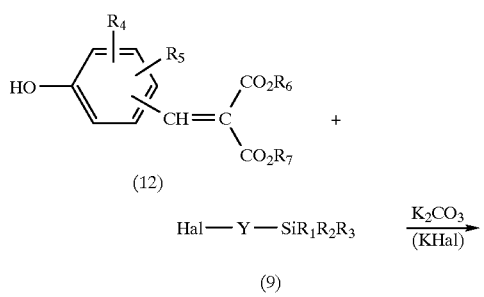

in which Y, $R_1$, $R_2$, $R_3$, $R_4$, $R_5$, $R_6$ and $R_7$ are as defined in formula (I) and Hal is a halogen, preferably chlorine.

The above syntheses present the advantage of being easier to carry out than hydrosilylation reactions.

Exemplary aromatic benzaldehyde derivatives include 4-hydroxybenzaldehyde or vanillin, which are commercially available products. Exemplary malonic ester derivatives include dimethyl malonate or diethyl malonate, which are also commercially available.

An exemplary hydroxybenzalmalonate derivative is dimethyl parahydroxybenzalmalonate marketed by ACROS.

And an exemplary silane halide derivative is chloropropyltrimethylsilane, marketed by WACKER.

By an "effective amount" of benzalmalonate silane according to the invention is intended an amount sufficient to provide a notable and significant improvement in the photostability of the dibenzoylmethane derivative(s) contained in the composition. The minimum amount of stabilizing agent to be employed, which can vary according to the nature of the cosmetically acceptable support (vehicle, diluent or carrier) reserved for the composition, can be determined without any difficulty by means of a conventional photostability measuring test, such as described in FR-A-2,607,700.

The benzalmalonate silanes are generally present in the compositions according to the invention in a content at least equal to 0.5% by weight, with respect to the total weight of the composition. More preferably, this amount ranges from 0.5% to 20% by weight, with respect to the total weight of the composition.

The cosmetic and/or dermatological compositions of this invention can, of course, contain one or more hydrophilic or lipophilic complementary screening agents active in the UV-A and/or UV-B (absorbers) ranges. These complementary sunscreens are advantageously selected from among cinnamic derivatives, the salicylic derivatives, the benzylidene camphor derivatives, the benzimidazole derivatives, the triazine derivatives, the benzophenone derivatives, the β,β'-diphenylacrylate derivatives, the p-aminobenzoic acid derivatives, the sunscreen polymers and filtering silicones described in WO-93/04665. Other examples of organic sunscreens are described in EP-A-487,404.

The compositions according to the invention can also contain artificial skin bronzing and/or browning agents (self-tanning agents) such as, for example, dihydroxyacetone (DHA).

The cosmetic and/or dermatological compositions of this invention can also contain pigments or nanopigments (average size of the primary particles: generally ranging from 5 nm to 100 nm, preferably from 10 and 50 nm) of coated or un-coated metallic oxides such as, for example, nanopigments of titanium dioxide (amorphous or crystallized in rutile and/or anatase form), of iron, of zinc, of zirconium, or of cerium, which are all photoprotective agents per se well known and acting by physical blocking (reflection and/or diffusion) of the UV radiation. Conventional coating agents are, in addition, alumina and/or aluminum stearate. Such nanopigments of metallic oxides, coated or un-coated, are described, in particular, in EP-A-518,772 and EP-A-518,773.

The compositions of the present invention can additionally comprise conventional cosmetic adjuvants and additives, especially selected from among fatty substances, organic solvents, ionic or non-ionic thickeners, softeners, antioxidants, anti-free radical agents, opacifiers, stabilizers, emollients, silicones, a-hydroxy acids, anti-foaming agents, hydrating agents, vitamins, perfumes, preservatives, surfactants, fillers, sequestrants, polymers, propellants, insect repellents, basifying or acidifying agents, colorants, dyes, pigments, or any other ingredients usually used in the cosmetic and/or dermatological field, in particular for the formulation of sunscreen compositions as emulsions.

The fatty substances can be an oil or a wax or mixtures thereof. By "oil" is intended a compound which is liquid at ambient temperature. By "wax" is intended a solid or substantially solid compound at ambient temperature, whose melting point is generally greater than 35° C.

Exemplary oils include mineral oils (vaseline); vegetable oils (sweet almond oil, macadamia oil, blackcurrant seed oil, jojoba oil); synthetic oils such as perhydrosqualene, alcohols, fatty acids or esters (such as benzoates of $C_{12}$–$C_{15}$ alcohols marketed under the trademark "Finsolv TN" by Finetex, octyl palmitate, isopropyl lanolate, trigylcerides including those of capric/caprylic acids), oxyethylene or oxypropylene fatty esters and ethers; silicone oils (cyclomethicone, polydimethylsiloxanes or PDMS) or fluorinated oils, polyalkylenes.

Exemplary waxy compounds include paraffin, carnauba wax, beeswax, hydrogenated castor oil.

Exemplary organic solvents include the lower alcohols and polyols.

And exemplary thickeners are crosslinked polyacrylic acids, guar gums and modified or unmodified celluloses such as hydroxypropylated guar gum, methylhydroxyethylcellulose and hydroxypropylmethylcellulose.

It will of course be appreciated that one skilled in this art will take care to select the possible complementary compound(s) indicated above (in particular the complementary sunscreens and/or the amounts thereof such that the advantageous properties intrinsically associated with the compositions of the invention will not, or will not substantially be, altered by the additions envisioned.

The compositions according to the invention can be formulated according to the techniques well know to this art, in particular those intended for the preparation of emulsions of oil-in-water or water-in-oil type.

The subject compositions are advantageously formulated in simple or complex emulsion form (W/O, O/W, O/W/O or W/O/W) such as a cream, a milk, or in the form of a gel or of a cream gel, a powder, a solid stick and can optionally be presented as an aerosol and be present in the form of foam or of spray.

Preferably, the compositions according to the invention are formulated as oil-in-water emulsions.

When an emulsion is concerned, the aqueous phase of this can comprise a non-ionic vesicle dispersion prepared according to known techniques (Bangham, Standish and Watkins, *J. Mol. Biol.*, 13, 238 (1965), FR-2,315,991 and FR-2,416,008).

The cosmetic and/or dermatological compositions of the invention are useful photoprotective compositions for the human epidermis or hair against ultraviolet radiation, as sunscreen compositions or as a makeup product.

When the cosmetic compositions according to the invention are used for the protection of the human epidermis against UV rays, or as sunscreen compositions, they can be formulated in suspension or dispersion form in solvents or fatty substances, in non-ionic vesicle dispersion form, or, alternatively, in emulsion form, preferably of oil-in-water type, such as a cream or a milk, a lotion, gel, cream gel, ointment, solid tube, stick, aerosol mousse or spray.

When the cosmetic compositions according to the invention are used for the protection of the hair, same can be formulated as a shampoo, lotion, gel, emulsion, non-ionic vesicle dispersion, hair lacquer and can constitute, for example, a composition for rinsing, to be applied before or after shampooing, before or after coloring or bleaching, before, during or after permanent waving or straightening, a styling or treating lotion or gel, a lotion or a gel for blowdrying or hairsetting, a permanent wave or a straightening, coloring or bleaching composition for the hair.

When the compositions are used as makeup products for the eyelashes, eyebrows or the skin, such as a cream for the treatment of the epidermis, foundation cream, lipstick, eyeshadow, blusher, mascara or eyeliner, same may be formulated in anhydrous or aqueous, solid or pasty form, such as oil-in-water or water-in-oil emulsions, non-ionic vesicle dispersions, or, alternatively, suspensions.

The sunscreen formulations in accordance with the invention are advantageously formulated with a support of oil-in-water emulsion type, the aqueous phase (especially comprising the hydrophilic sunscreens) generally constitutes from 50% to 95% by weight, preferably from 70% to 90% by weight, with respect to the total weight of the formulation, the oily phase (especially comprising the lipophilic sunscreens) from 5% to 50% by weight, preferably from 10% to 30% by weight, with respect to the total weight of the formulation, and the (co)emulsifier(s) from 0.5% to 20% by weight, preferably from 2% to 10% by weight, with respect to the total weight of the formulation.

In order to further illustrate the present invention and the advantages thereof, the following specific examples are given, it being understood that same are intended only as illustrative and in nowise limitative.

EXAMPLE 1

Preparation of dimethyl 2-[3-methoxy-4-(3-trimethylsilanylpropyloxy)benzylidene]malonate
(according to reaction scheme A)

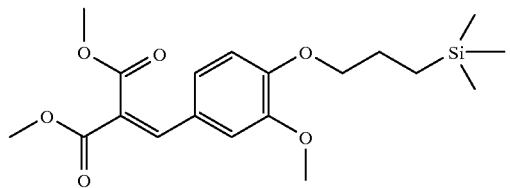

(a) First step: preparation of 3-methoxy-4-(3-trimethylsilanylpropyloxy)benzaldehyde 3-Chloropropyltrimethylsilane (33.14 g, 0.22 mol) was added dropwise over the course of 20 minutes into a mixture of vanillin (30.4 g, 0.2 mol) and potassium carbonate (30.4 g, 0.22 mol) in 150 ml of dry dimethylformamide (DMF) heated to 50° C. under nitrogen. The mixture was maintained for 4 hours at 95°–110° C. The reaction mixture was cooled and poured into ice water. The aqueous phase was extracted 3 times with dichloromethane. The organic phases were dried over sodium sulfate and concentrated in vacuo. After distillation in vacuo (0.04 mm Hg), 47.5 g (yield: 89%) of 3-methoxy-4-(3-trimethylsilanylpropyloxy) benzaldehyde were obtained in the form of a slightly pink oil distilling at 112°–114° C. and employed as such in the following step (b).

(b) Second step: preparation of dimethyl 2-[3-methoxy-4-(3-trimethylsilanylpropyloxy)benzylidene]malonate A mixture of the compound prepared in step (a) (13.3 g, 0.05 mol) and of dimethyl malonate (7.93 g, 0.06 mol) in 20 ml of toluene was heated to reflux for 3 hours in the presence of 0.5 ml of piperidine and 0.3 ml of acetic acid. The reaction mixture was cooled and poured into water and then extracted with diisopropyl ether. The organic phase was dried over sodium sulfate and concentrated. After crystallization in a 90:10 by volume methanol/water mixture, 15 g (yield: 79%) of the compound having the following characteristics were obtained:

(i) white powder
(ii) m.p.: 51°–52° C.
(iii) UV (Ethanol) $\lambda_{max}$=331 nm, $\epsilon_{max}$=20,300
Elemental analysis for $C_{19}H_{28}O_6Si$
theory: C: 59.97 H: 7.42 Si: 7.38
found: C: 59.80 H: 9.35 Si: 7.30

EXAMPLE 2

Preparation of diethyl 2-[4-(3-trimethylsilanylpropyloxy)benzylidene]malonate
(according to reaction scheme B):

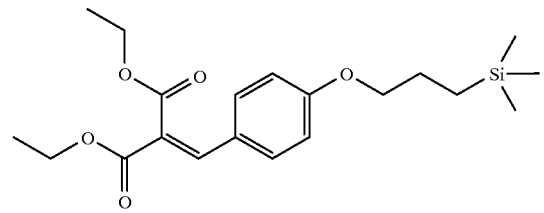

3-Chloropropyltrimethylsilane (16.57 g, 0.11 mol) was added dropwise over the course of 10 minutes into a mixture of diethyl 4-hydroxybenzalmalonate (15.18 g, 0.11 mol) and potassium carbonate (15.18 g, 0.11 mol) in 100 ml of dry DMF heated to 80° C. under nitrogen. The mixture was maintained for 3 hours, 30 minutes, at 120°–130° C. The reaction mixture was then cooled and poured into ice water. The aqueous phase was extracted 2 times with dichloromethane. The organic phases were washed with water and then dried over sodium sulfate and concentrated in vacuo. After crystallization in methanol, 31.6 g (yield: 76%) of the compound having the following characteristics were obtained:

(i) white powder
(ii) m.p.: 34°–35° C.
(iii) UV (Ethanol) $\lambda_{max}$=314 nm, $\epsilon_{max}$=26,400
Elemental analysis for $C_{20}H_{30}O_5Si$
theory: C: 63.46 H: 7.99 Si: 7.42
found: C: 63.31 H: 7.90 Si: 7.50

Thus, it has been determined that the benzalmalonate silane obtained above stabilized 4-tert-butyl-4'-methoxydibenzoylmethane with respect to ultraviolet radiation in such manner that was at least as efficacious as the benzalmalonate siloxanes described in EP-A-0,709,080.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the UV-photoprotection of human skin and/or hair, comprising (a) an effective UV-photoprotecting amount of at least one dibenzoylmethane UV-sunscreen compound and (b) an effective dibenzoylmethane compound (a) photostabilizing amount of at least one benzalmalonate silane having the structural formula (I):

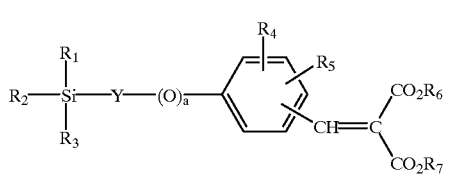

(I)

in which $R_1$, $R_2$ and $R_3$, which may be identical or different, are each an optionally halogenated $C_1$–$C_{10}$ alkyl radical or a phenyl radical; $R_4$ and $R_5$, which may be identical or different, are each a hydrogen atom, a hydroxyl group, a $C_1$–$C_6$ alkyl radical, a $C_1$–$C_6$ alkoxy radical, or a trimethylsilyloxy radical; $R_6$ and $R_7$, which may be identical or different, are each a $C_1$–$C_8$ alkyl radical; a is equal to 0 or 1; and Y is a divalent radical having one of the following formulae (1) to (4):

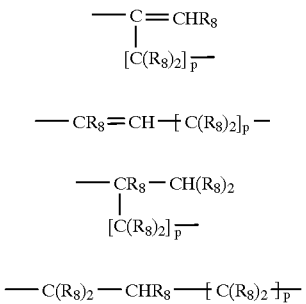

wherein $R_8$ is a hydrogen atom or a $C_1$–$C_5$ alkyl radical, and l is an integer ranging from 1 to 10, inclusive, with the proviso that the group —Y—(O)$_a$— and the two radicals $R_4$ and $R_5$ are variously bonded to the aromatic ring member in the para-position and in the two meta-positions with respect to the radical —CH=C—[(CO$_2$R$_6$)](CO$_2$R$_7$).

2. The sunscreen/cosmetic composition as defined by claim 1, formulated with a topically applicable, cosmetically/dermatologically acceptable vehicle, diluent or carrier therefor.

3. The sunscreen/cosmetic composition as defined by claim 1, wherein formula (I) at least one of the following conditions is satisfied:

$R_1$ is methyl;
$R_2$ is methyl or ethyl;
$R_3$ is methyl;

Y is a divalent radical of formula (3) or (4) in which $R_8$ is hydrogen or methyl and p is 1 or 2;
a is 1;
$R_4$ is hydrogen or a methoxy radical;
$R_5$ is hydrogen;
$R_6$ is methyl or ethyl;
$R_7$ is methyl or ethyl; and/or
the —Y—(O)$_a$— group is bonded to the aromatic ring member in the para-position with respect to the —CH=C—[(CO$_2$R$_6$)](CO$_2$R$_7$) radical.

4. The sunscreen/cosmetic composition as defined by claim 1, said at least one benzalmalonate silane (I) having one of the following formulae (5), (6) or (7):

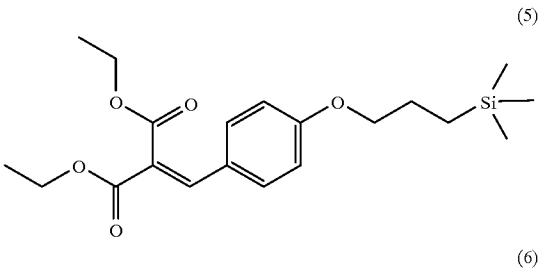

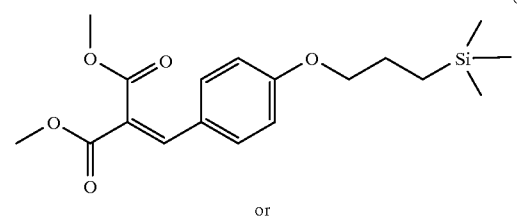

or

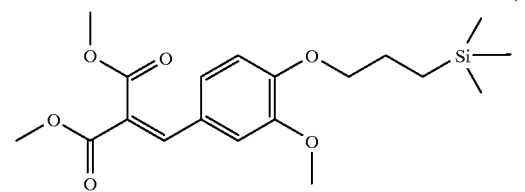

5. The sunscreen/cosmetic composition as defined by claim 1, said at least one dibenzoylmethane compound comprising 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxy-dibenzoylmethane, and/or 4,4'-dimethoxydibenzoylmethane.

6. The sunscreen/cosmetic composition as defined by claim 5, said at least one dibenzoylmethane compound comprising 4-tert-butyl-4'-methoxydibenzoylmethane.

7. The sunscreen/cosmetic composition as defined by claim 5, said at least one dibenzoylmethane compound comprising 4-isopropyldibenzoylmethane.

8. The sunscreen/cosmetic composition as defined by claim 1, comprising from 0.5% to 20% by weight of said at least one benzalmalonate silane (I).

9. The sunscreen/cosmetic composition as defined by claim 1, further comprising at least one additional hydrophilic or lipophilic organic UV-A and/or UV-B sunscreen.

10. The sunscreen/cosmetic composition as defined by claim 1, further comprising at least one active agent for the artificial tanning and/or browning of human skin.

11. The sunscreen/cosmetic composition as defined by claim 1, further comprising at least one additive or adjuvant which comprises a fat, organic solvent, ionic or nonionic thickening agent, softener, antioxidant, anti-free radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, pigment, nanopigment, or mixture thereof.

12. The sunscreen/cosmetic composition as defined by claim 1, comprising a nonionic vesicle dispersion, emulsion, cream, milk, gel, cream gel, ointment, suspension, dispersion, powder, solid, stick, foam or spray.

13. The sunscreen/cosmetic composition as defined by claim 1, comprising a makeup.

14. The sunscreen/cosmetic composition as defined by claim 1, comprising an anhydrous or aqueous solid or paste, emulsion, suspension, or dispersion.

15. The sunscreen/cosmetic composition as defined by claim 1, comprising a shampoo, lotion, gel, emulsion, nonionic vesicle dispersion, hair lacquer, or rinse.

16. The sunscreen/cosmetic composition as defined by claim 1, comprising a skin cream, foundation, face powder, lipstick, mascara, eyeliner, hair gel, hair lotion, or shampoo.

17. A method for protecting human skin and/or hair against the deleterious effects of ultraviolet irradiation, comprising topically applying thereto an effective amount of the sunscreen/cosmetic composition as defined by claim 1.

18. A method for protecting human skin and/or hair against the deleterious effects of solar radiation, comprising topically applying thereto an effective amount of the sunscreen/cosmetic composition as defined by claim 1.

* * * * *